United States Patent [19]

Yin

[11] 4,148,314
[45] Apr. 10, 1979

[54] BLOOD PRESSURE ALARM SYSTEM FOR DIALYSIS MACHINES

[75] Inventor: Chieh-Kung Yin, Lindenhurst, Ill.

[73] Assignee: Baxter Travenol Laboratories, Inc., Deerfield, Ill.

[21] Appl. No.: 733,585

[22] Filed: Oct. 18, 1976

[51] Int. Cl.² ............................................. A61M 1/03
[52] U.S. Cl. ........................ 128/214 E; 128/DIG. 13; 210/90
[58] Field of Search ......... 128/214 E, 214 F, DIG. 1, 128/DIG. 3, DIG. 12, DIG. 13, 2.05 R, 2.05 A, 214 R, 214 B, 2.05 D; 23/258.5, 258.5 R; 210/22 A, 22 C, 22 D, 90, 321 A, 321 B, 22, 85, 321 R

[56] References Cited

U.S. PATENT DOCUMENTS

| | | | |
|---|---|---|---|
| 3,636,941 | 1/1972 | Gueurekian | 128/2.05 A |
| 3,655,095 | 3/1972 | Kienitz | 128/214 E |
| 3,756,234 | 9/1973 | Kopp | 128/214 R |
| 3,814,082 | 6/1974 | Taylor | 128/2.05 R |
| 3,830,234 | 8/1974 | Kopp | 128/214 R |
| 3,868,679 | 2/1975 | Arneson | 340/347 AD |
| 3,871,360 | 3/1975 | Van Horn et al. | 128/2.05 R |
| 3,915,156 | 10/1975 | Wasfl et al. | 128/2.05 Q |
| 3,939,824 | 2/1976 | Arneson et al. | 128/2.05 A |
| 3,946,731 | 3/1976 | Lichtenstein | 128/214 R |
| 3,996,928 | 12/1976 | Marx | 128/2.05 Q |
| 4,008,617 | 2/1977 | Yen et al. | 73/362 AR |

OTHER PUBLICATIONS

Barnes, R. et al., "An Automated Tilting Bed for Continuous Control of Blood Pressure," IEEE Trans. on Biomed. Engr., vol. BME-21, #2, pp. 124–129, 3/74.

Primary Examiner—Robert W. Michell
Assistant Examiner—Francis J. Jaworski
Attorney, Agent, or Firm—Paul C. Flattery; Gerald S. Geren

[57] ABSTRACT

There is disclosed herein a blood pressure alarm system for use in a dialysis machine whereby alarms may be activated, and a blood pump deactivated if the actual blood pressure increases above or decreases below predetermined levels. The levels are determined by setting a particular blood pressure point and setting the amount by which the pressure can vary above and below the set point; the range of variation is sometimes referred to as the alarm window. A digital memory is provided for storing the set point and preventing variation of the set point with time.

7 Claims, 7 Drawing Figures

BLOOD PRESSURE ALARM SYSTEM FOR DIALYSIS MACHINES

BACKGROUND OF THE INVENTION

This invention relates to dialysis machines of the type used in artificial kidney systems, and more particularly, to a blood pressure alarm system for use therein.

In a dialysis machine water and concentrate are mixed to provide dialysis solution which is delivered to a dialyzer through which both blood and dialysis solution flow on opposite sides of a semipermeable membrane. Waste products from the blood pass through the membrane into the dialysis solution for disposal. Normally dialysis takes approximately 4–6 hours.

Dialysis machines are equipped with both arterial and venous blood pressure alarm systems for activating an alarm and for deactivating a blood pump in the extracorporeal blood circuit in the event that the blood pressure in the blood circuit exceeds or falls below predetermined values. This is sometimes referred to as an alarm window. Proper monitoring of both the arterial and venous pressure is important since failure or errors in monitoring can result in blood loss from the patient.

One alarm monitoring system provides for alarm conditions when the blood pressure varies by more than ±50 mm/Hg from an adjustable and manually set pressure point. The pressure selector is a knob having an indicating arrow which is set with respect to pressure indicating markings on a face plate. A meter is provided which displays the actual pressure but not the selected pressure. A comparator is provided to compare actual pressure against the set point ±50 mm/Hg. This system had disadvantages in that: (1) the nurse could err in setting the reference point; (2) the face plate/knob relationship could be off which would result in an erroneously selected reference point; and (3) the machine characteristics could vary which would result in an erroneous reference point.

In an effort to overcome these problems, an unmarked plunger-type knob was provided which cooperates with the meter for the setting of the reference point. With the knob in the out position, the meter displays actual blood pressure and, when pushed to the in position, the meter is engaged and the reference point can be selected against the meter scale. The alarm is still set ±50 mm/Hg above and below the reference point. With this system the errors due to knob mounting and machine error are eliminated and the internal pressure transducer and alarm set knob referenced against the same meter. However, this system is inconvenient to operate since the knob has to be pushed in and out to set while watching the meter. Furthermore, the variability about the reference point could not be controlled.

In a third generation machine, provision is made to set the reference point using the pressure produced when the dialysis machine is operating and the patient's condition has stabilized. By moving a slide switch from a set-up mode to an operate mode, the reference point is set into the machine. This eliminates the need for the plunger-type knob, and a second slide control is provided by which the variability about the reference point can be adjusted between ±10 and ±100 mm/Hg. In this system a memory is provided which stores the reference point. The memory is essentially a capacitor, and the charge on the capacitor is updated every 5 minutes during dialysis by comparison against the actual blood pressure at that point in time, so long as no alarm condition had been met. The blood pressure at 5 minutes, 10 minutes, etc., can be different than the desired reference point. It should be noted that the variability is set against the memory point. Thus, changes in the charge on the capacitor could result in changes in the alarm conditions which would be undesirable.

It is therefore an object of this invention to provide a memory system for use in a blood pressure alarm system in a dialysis machine, wherein the alarm conditions remain fixed relative to their initial settings with time.

This and other objects will become apparent from the following description and appended claims.

SUMMARY OF THE INVENTION

There is provided by virtue of this invention an alarm circuit for use with a dialysis machine which alarms in response to blood pressure changes. A blood pressure sensing circuit in the alarm develops a pressure signal which varies in accordance with blood pressure. A memory receives the pressure signal and stores a digital signal corresponding to the pressure signal in a storage device. The memory includes circuitry which develops an analog memory signal corresponding to the stored digital signal. Pressure variation selection circuitry is also provided in the alarm, and it develops a variation signal representing blood pressure variation limits. Comparison circuitry in the alarm is connected to the blood pressure sensing circuit, the memory and the pressure variation selection circuitry. The comparison circuitry operates in response to a pressure signal greater than the analog memory signal plus the variation signal or a blood pressure signal less than the analog memory signal minus the variation signal, to develop a first comparison signal. Control circuitry operates in response to the first comparison signal to provide the noted alarm.

DETAILED DESCRIPTION OF THE PREFERRED EMBODIMENTS

Figure 1:
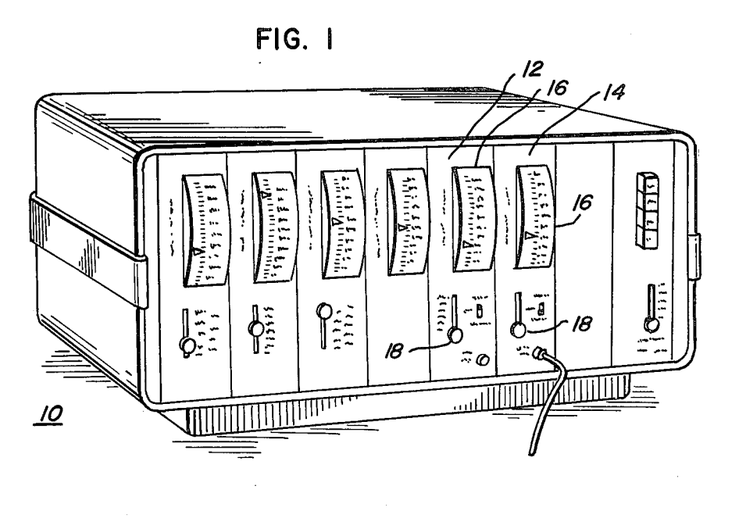
FIG. 1 is a perspective view of a dialysis machine of the type employing the alarm system of this invention.
Figure 2:
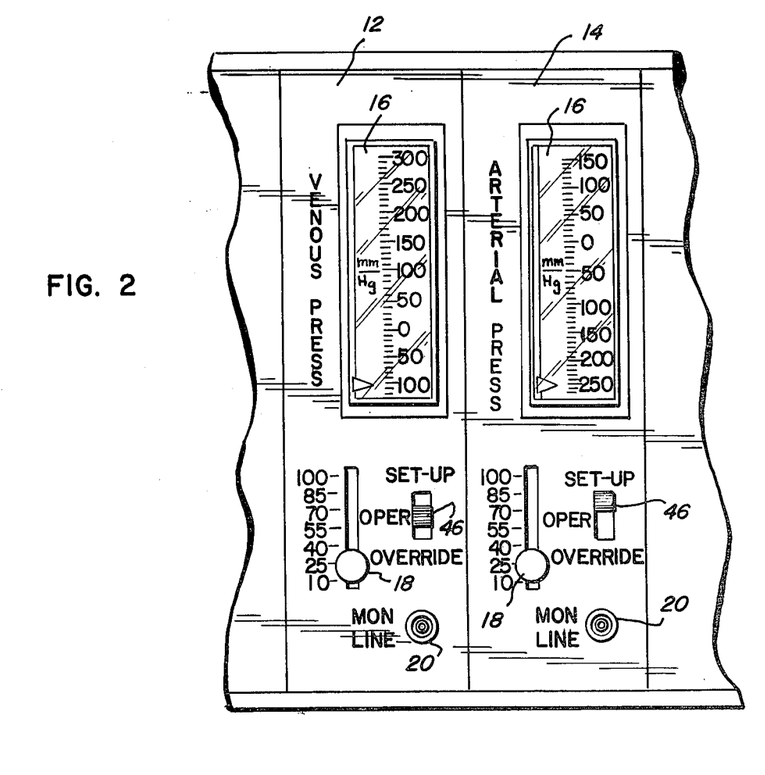
FIG. 2 is an enlarged view of a portion of the front panel of the machine showing the venous and arterial pressure controls.

Referring now to the drawings, a dialysis machine 10 generally includes a venous pressure module 12 and an arterial pressure module 14. Each module is substantially identical and includes a meter 16 for indicating blood pressure. A slide control 18 allows selection of an alarm window between ±10 mm/Hg and ±100 mm/Hg of the meter reading. A female connector 20 is provided for connection to a transducer to monitor blood pressure.

Since the arterial and venous modules are identical, the following description is in reference to the arterial module, it being understood that such description is applicable to the venous module.

Figure 3:
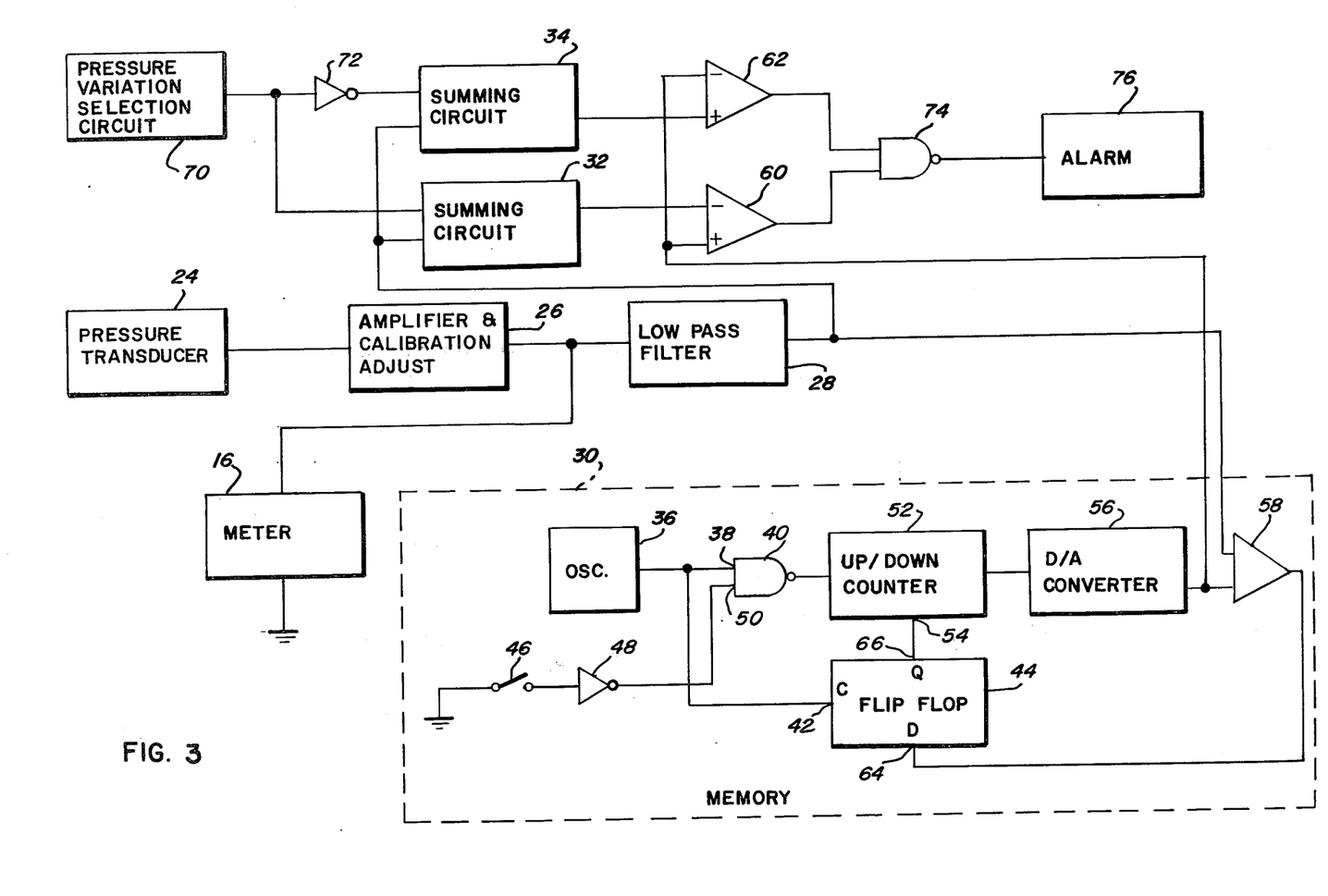
FIG. 3 is a block diagram of one embodiment of the alarm circuit of this invention.

Referring now to FIG. 3, the alarm circuit embodiment shown therein includes a pressure transducer 24 which attaches to the blood line between the patient and the dialysis machine. Pressure transducer 24 may be attached to the arterial blood line and then connected to the arterial module 14 by way of connector 20 (shown in FIG. 2). Pressure transducer 24 will sense the blood pressure in the attached line and develop pressure voltage which varies in accordance with the sensed pressure level. This pressure voltage is coupled to an amplifier and calibration adjusting circuit 26.

Amplifier and calibration adjusting circuit 26 amplifies the received pressure voltage and couples the amplified voltage to meter 16, where it may be observed, and to low pass filter 28. The calibration adjusting circuit portion of amplifier and calibration adjusting circuit 26, in conjunction with meter 16, allows the manufacturer to calibrate the meter 16 against a pressure reference for any different pressure transducer 24 which may be utilized with machine 10.

The amplified pressure voltage coupled to low pass filter 28 is considered a DC signal even though it does vary in accordance with variations in pressure. The variations in pressure, however, are very slow variations and are non-periodic. Noise signals, such as may be developed by the ballasts in fluorescent lamps and as a result of a person's heart beats, may be sensed by pressure transducer 24 or coupled directly to the circuitry resulting in an AC-type signal added to the amplified DC pressure voltage. Low pass filter 28 operates to attenuate signals in excess of one-half cycle per second so that the DC amplified pressure voltage will pass through the low pass filter 28 with substantially no attenuation whereas the AC signals will be substantially attenuated. The amplified filtered pressure voltage from low pass filter 28 is coupled to a memory circuit 30, represented by dash lines, and to first and second summing circuits 32 and 34, respectively.

Memory circuit 30 includes an oscillator 36 which operates continuously to develop clock pulses which are coupled to one input 38 of NAND gate 40 and to the clock input 42 of a bistable multivibrator 44, more commonly known as a flip/flop.

A switch 46 is connected between ground potential and the input of inverter amplifier 48, the output of which is coupled to the second input 50 of NAND gate 40. When switch 46 is closed, the clock pulses developed by oscillator 36 are coupled through NAND gate 40 to an up/down counter 52.

Up/down counter 52 either adds or subtracts each clock pulse received from a digital count stored therein in accordance with the state of an up/down control signal coupled to up/down control input 54. The digital count stored in up/down counter 52 is coupled to a digital to analog (D/A) converter 56 which develops an analog memory signal corresponding to the digital count signal in counter 52. The analog memory signal developed by D/A converter 56 is converted to a voltage and coupled to one input of a comparator 58 in memory 30 and to comparators 60 and 62.

In operation, dialysis machine 10 is connected to the patient, and pressure transducer 24 is connected to the arterial line. The signal developed by pressure transducer 24 is coupled through amplifier and calibration adjusting circuit 26 and low pass filter 28 so that an amplified filtered pressure voltage is coupled to one input of comparator 58. Assuming that the machine has just been initialized and no count is recorded in counter 52, the output voltage from converter 56 is less than the pressure voltage from low pass filter 28. Consequently, comparator 58 develops a high state or one level signal indicating that the pressure voltage is greater than the analog memory voltage at the output of converter 56. The high state signal is coupled to the D input of flip/flop 44. Upon receipt of the next clock pulse at clock input 42, flip/flop 44 samples the high state signal at D input 64 and develops a high state signal at the Q output 66. The high state signal developed at the Q output 66 is coupled to up/down control input 54 of counter 52 causing counter 52 to count up adding each clock pulse received to the stored digital count.

It is to be understood that the above and following operation is described with respect to a pressure voltage greater than an analog memory voltage from converter 56. If the pressure voltage is less than the analog memory voltage, a low state signal is developed by comparator 58 and coupled to flip/flop 44. This results in a low state signal being coupled to the up/down control input 54 of counter 52 which sets counter 52 to count down, subtracting each clock pulse received from the stored digital count.

When machine operation is initialized, the switch 46 is in the "set-up" position. The "set-up" position connects ground potential to inverter amplifier 48 through switch 46. With ground potential at its input, a high state signal is coupled to input 50 of NAND gate 40 allowing clock pulses developed by oscillator 36 to be coupled to counter 52. Counter 52 is set to count up, as previously noted, adding each clock pulse received to the stored digital count, so that it begins counting and increasing the digital count stored therein. As the count increases, the analog memory voltage developed by D/A converter 56 increases. The analog memory voltage increases until it reaches and exceeds the pressure voltage coupled from low pass filter 28 to comparator 58. When the analog memory voltage exceeds the pressure voltage, the output of comparator 58 will change from a high to a low state. At the next clock pulse, the Q output 66 of flip/flop 44 will change from a high to low state, and counter 52 will begin to count down, subtracting each clock pulse from the digital count stored therein. This will result in a slightly reduced voltage at the output of D/A converter 56. If the analog memory voltage now is below the pressure voltage, comparator 58 again will develop a high state signal at its output.

The hunting process, whereby the analog memory voltage goes slightly above and below the pressure voltage, continues as long as switch 46 remains closed. Because of the oscillator frequency, the hunting or switching occurs very rapidly. Because of the speed at which hunting occurs and the precision of comparator 58, the analog memory voltage developed differs only very slightly from the pressure voltage. When the patient's condition stabilizes, the technician observing the patient and meter 16 recognizes that the patient's condition has stabilized and the machine is operating properly as indicated by the blood line pressure shown on meter 16. The technician then moves switch 46 to the operate position so that ground potential is removed and clock pulses no longer can be coupled through NAND gate 40 to up/down counter 52. The count last stored is now held in counter 52, and a corresponding analog memory voltage is developed by D/A converter 56. The above-described operation is similar to a tracking analog/digital servo system. Such a system operation in a memory to inhibit clock pulses has not previously been provided.

Slide control 18 shown in FIGS. 1 and 2 is a part of a pressure variation selection circuit 70 in FIG. 3. Pressure variation selection circuit 70 will develop an output voltage whose amplitude is adjustable to correspond to the desired blood pressure limits, adjustments being provided by slide control 18. In the embodiment shown, if a blood pressure variation of 10 mm/Hg above and below the selected blood pressure is desired, slide control 18 is moved to the line adjacent the number 10, and a very low voltage is developed by pressure variation selection circuit 70 corresponding to the pressure change of 10 mm/Hg above or below the preselected nominal pressure stored in digital form in memory 30. Should a limit of ±100 mm/Hg be desired, slide control 18 is moved to the ±100 line and the output voltage developed by pressure variation selection circuit 70 increases to represent the pressure variation of ±100 mm/Hg. Pressure variation selection circuit 70 allows selection of an upper and lower limit, or window, in which the blood pressure can vary without operation of the alarm. If the blood pressure monitored by transducer 24 exceeds or falls below the limits, an alarm occurs.

The output voltage developed by pressure variation selection circuit 70 is coupled to a second input of summing circuit 32 and, through an inversion amplifier 72, to the second input of summing circuit 34. Because of the relative polarities of the pressure voltage and of the pressure variation selection voltage, the voltages coupled to summing circuit 34 are substracted, inverted and the resultant summed inverted voltage is coupled to the plus input of comparator 62. The voltages coupled to the summing circuit 32 are added, inverted and the resultant summed inverted voltage is coupled to the negative input of comparator 60.

If the pressure sensed by pressure transducer 24 increases, the voltage coupled to summing circuit 34 increases, becoming more positive and causing the voltage coupled to the positive input of comparator 62 to become negative. When the pressure sensed by pressure transducer 24 exceeds the limit selected in pressure variation selection circuit 70, the voltage coupled to the positive input of comparator 62 falls below the analog memory voltage coupled from memory circuit 30 to the negative input of comparator 62, causing comparator 62 to develop a low state signal at its output. The low state signal developed by comparator 62 is coupled to one input of a NAND gate 74 which operates in response to the received low state signal to develop a high state signal at its output. An alarm circuit 76 is connected to the output of NAND gate 74 and operates in response to the received high state signal to provide audible and visual alarms and to inhibit further operation of the blood pump, thereby terminating the blood flow from the patient through the dialysis machine.

If the pressure sensed by pressure transducer 24 decreases, indicating a possible leak or break in the line between the patient and the machine or a possible patient problem, the pressure voltage coupled to summing circuit 32 decreases. This produces an increase in the resultant voltage developed by summing circuit 32. Consequently, the voltage coupled to the negative input of comparator 60 becomes more positive. When the pressure sensed by pressure transducer 24 decreases below the lower limit of the pressure variation window selected in pressure variation selection circuit 70, the summed voltage developed by summing circuit 32 and coupled to the negative input of comparator 60 rises above the analog memory voltage coupled to the positive input of comparator 60 and causes comparator 60 to develop a low state signal at its output. The low state signal is coupled to a second input of NAND gate 74, which operates in response to the low state signal to develop a high state signal at its output. The high state signal is coupled to alarm circuit 76 actuating the alarm and deactivating the blood pump.

Figure 4:
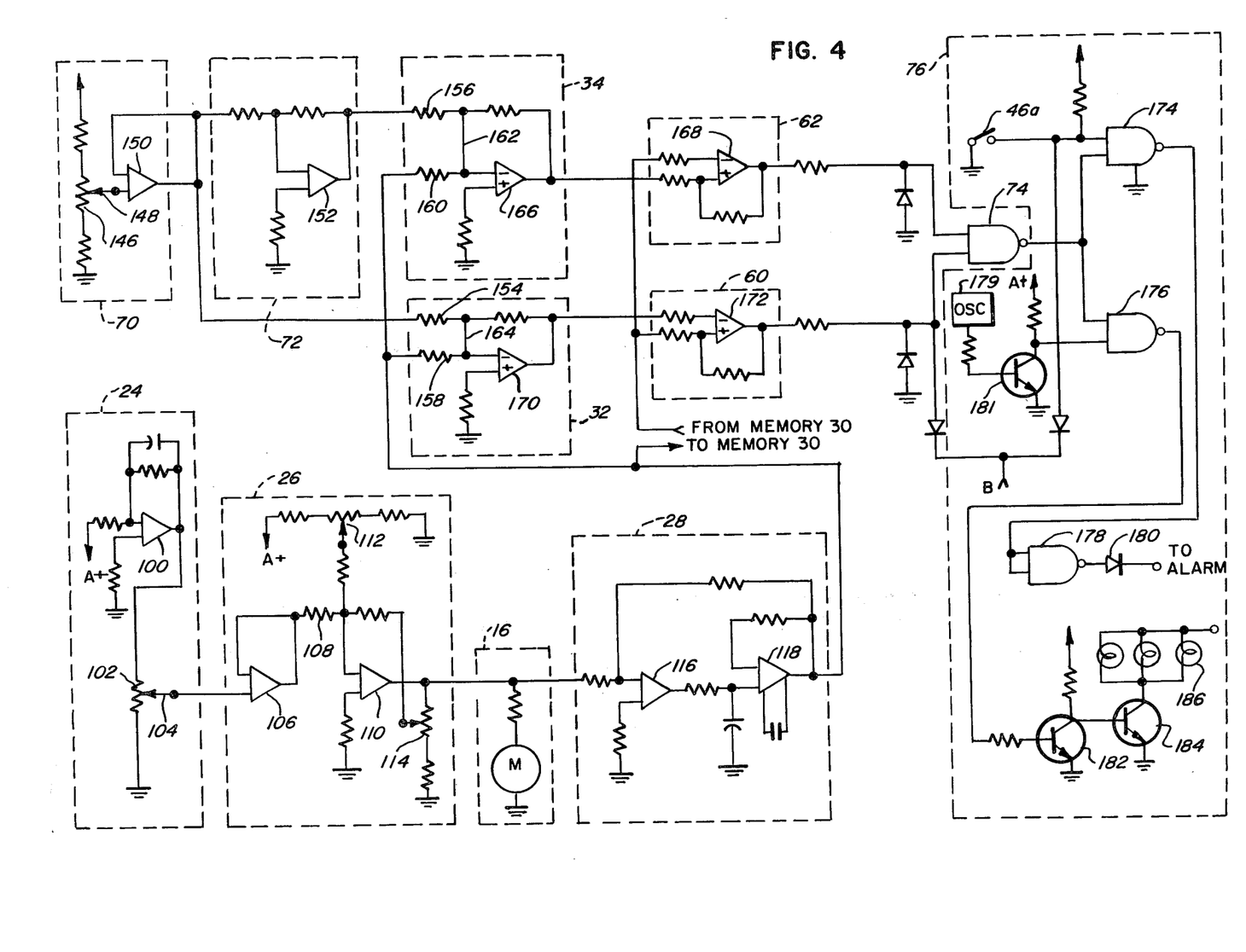
FIG. 4 is a schematic diagram of a portion of the alarm circuit represented in block diagram form in FIG. 3.

Referring now to FIG. 4, pressure transducer 24 includes a constant voltage generator 100 coupled to a potentiometer 102. The potentiometer 102 is connected to an arterial blood line in dialysis machine 10 by way of a pressure sensitive diaphragm connected to arm 104 of potentiometer 102. Changes in pressure cause movement of arm 104. With a constant voltage supplied to potentiometer 102 by constant voltage generator 100, the movement of potentiometer arm 104 causes a change in the voltage level coupled to a buffer amplifier 106 in amplifier and calibration adjusting circuit 26.

Buffer amplifier 106 acts to isolate potentiometer 102 from the following circuitry, and couples the voltage signal received through resistor 108 to a gain control and offset control amplifier 110. Potentiometer 112 and potentiometer 114, connected to gain control and offset control amplifier 110, allow adjustment of the circuit for a proper zero and full scale. These potentiometers and gain control amplifier 110 are set by first applying a pressure corresponding to a minimum reading on meter 16 to potentiometer 102 so that a minimum voltage signal is coupled to and through buffer amplifier 106. Potentiometer 112 then is set so that meter 16 indicates zero on the scale. Then the maximum pressure represented on meter 16 is applied to pressure transducer 24 so that potentiometer 102 couples a maximum voltage signal to and through buffer amplifier 106 to gain control and offset control amplifier 110. With maximum pressure applied, potentiometer 114 is adjusted so that meter 16 provides a full scale indication.

In normal operation, when pressure transducer 24 is attached to the blood line, the voltage signal developed at the output of amplifier 110 is somewhere between the voltage limits corresponding to the minimum and maximum meter reading set by potentiometers 112 and 114. This voltage signal is coupled to meter 16 for visual presentation and to and through low pass filter 28. Low pass filter 28 includes a first amplifier 116 which receives the voltage signal from amplifier 110, and a second amplifier 118 whose input in coupled to the output of amplifier 116. Amplifiers 116 and 118 are interconnected in a typical low pass filter configuration and operate as previously described to eliminate extraneous high frequency components. The filtered signal passed by low pass filter 28 is coupled to memory circuit 30, shown in greater detail in FIG. 4a, and to summing circuits 32 and 34.

Figure 4A:
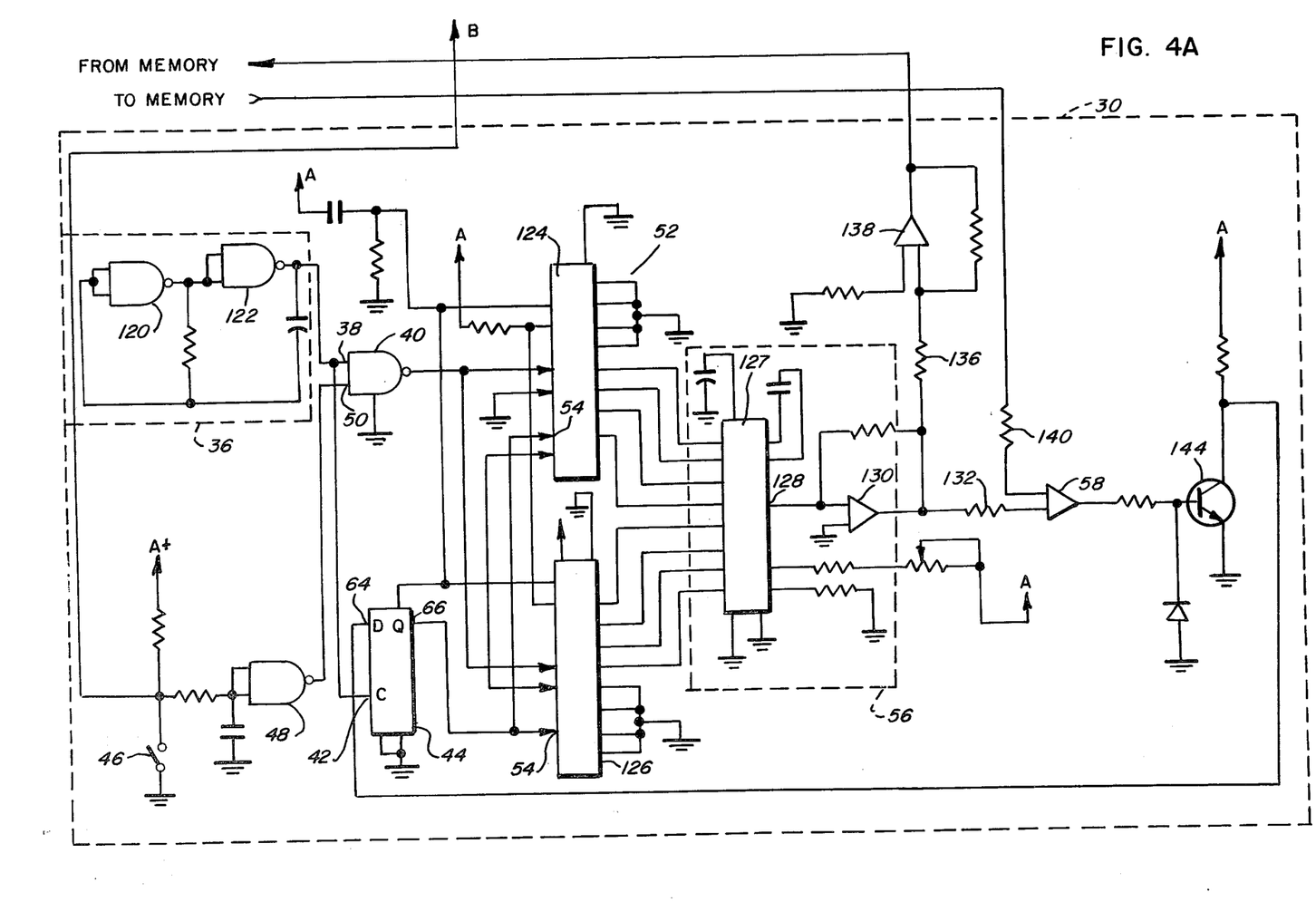
FIG. 4a is a schematic diagram of a second portion of the alarm circuit in FIG. 3.

Referring to FIG. 4a, NAND gates 120 and 122 are interconnected to form oscillator 36 in memory 30. The clock pulses developed by oscillator 36 are coupled from the output of NAND gate 122 to input 38 of NAND gate 40 and to the clock input 42 of flip/flop 44.

Inverter 48, shown in FIG. 3, is shown in FIG. 4a as a two-input NAND gate with both inputs connected together. When switch 46 is opened, a high state signal is coupled to the inputs of NAND gate 48 so that a low state signal is developed at its output and coupled to second input 50 of NAND gate 40. With a low state signal at second input 50 of NAND gate 40, it develops and maintains a high state signal at its output notwithstanding the clock pulses coupled from oscillator 36 to first input 38. When switch 46 is closed, a high state signal is coupled to input 50 of NAND gate 40. With a high state signal appearing at second input 50, the output of NAND gate 40 will switch between a high and low state signal in response to each clock pulse, thus developing clock pulses that correspond to the clock pulses coupled from oscillator 36. The clock pulses developed at the output of NAND gate 40 are coupled to the clock inputs of first and second counter portions 124 and 126 in up/down counter 52.

Each first and second counter portion 124 and 126 is a four-stage COS/MOS presettable up/down counter, such as is available from the RCA Solid State Division under the part number CD4029AE. Each counter portion will count up or down in accordance with the signal at its control input, and is capable of counting up to $2^4 - 1$ and down to zero. When first and second counter portions 124 and 126 are connected serially, as shown, they are capable of counting from zero to $2^8 - 1$. The count is stored in the first and second counter portions 124 and 126 as a digital number in the form of a series of ones and zeros, and it is this series of digits which is coupled in parallel from first and second counter portions 124 and 126 to converter 127 in D/A converter 56.

Converter 127 may, for example, be an eight-bit multiplying digital to analog converter, such as is available from Motorola Semiconductor Products, Inc., under the part number MC1408L-8. Converter 127 receives the binary number from counter 52 and converts the binary number to an analog current whose amplitude is proportional to the received binary number. This analog current is coupled from output 128 of converter 127 to a current to voltage converter 130.

Current to voltage converter 130 develops an output voltage whose amplitude corresponds to the amplitude of the current received from output 128 of converter 127, so that it is the analog equivalent of the digital number stored in counter 52. The analog memory voltage developed at the output of converter 130 is coupled from D/A converter 56, through resistor 132 to an input of comparator 158, and through resistor 136 to inverter 138. Inverter 138 inverts the received voltage and develops a corresponding voltage inverted in sign at its output. In the preferred embodiment, the voltage developed at the output of inverter 138 is a negative voltage. This voltage is coupled to comparators 60 and 62 shown in FIGS. 3 and 4.

The output of low pass filter 28 coupled to memory 30 is coupled through resistor 140 to one input of comparator 58, and as noted, the analog memory voltage is coupled through resistor 132 to the second input of comparator 58. These two voltages are compared in comparator 58. If the voltage coupled through resistor 140 exceeds the voltage coupled through resistor 132, the output of comparator 58 is a low state signal. This low state signal is inverted by a level shifting transistor 144 in comparator 58 and coupled to the D input 64 of flip/flop 44. Upon receipt of the following clock pulse, a high state signal is developed at the Q output 66 and coupled to control input 54 of counter portions 124 and 126, causing them to count up or add in response to each clock pulse.

When the voltage coupled through resistor 132 exceeds the voltage coupled through resistor 140, comparator 58 develops a high state signal at its output. This high state signal is inverted by level shifting transistor 144 and coupled to the D input 64 of flip/flop 44, and upon receipt of the next following clock pulse, flip/flop 44 changes states and develops a low state signal at Q output 66. The low state signal is coupled to control input 54 of counter portions 124 and 126, causing these portions to count down or subtract in response to each clock pulse. Further details of the memory operation have been described previously.

Referring again to FIG. 4, pressure variation selection circuit 70 includes a potentiometer 146 coupled between supply potential and ground potential. Slide control 18, shown on FIGS. 1 and 2, is connected to arm 148 of potentiometer 146 and allows selection of the desired upper and lower limit voltage as previously described. The voltage selected is coupled through arm 148 through a buffer amplifier 150 to amplifier 152 in inversion amplifier 72, and to the summing resistor 154 in summing circuit 32. Amplifier 152 inverts the received voltage and couples the inverted voltage to resistor 156 in summing circuit 34.

The pressure voltage developed at the output of low pass filter 28 is coupled to summing resistor 158 in summing circuit 32 and to summing resistor 160 in summing circuit 34. Resistors 156 and 160 are connected together at summing junction 162 and summing resistors 154 and 158 are connected together at summing junction 164. The voltages coupled to summing resistors 156 and 160 are summed at summing junction 162, and this summed voltage is amplified and inverted by amplifier 166 and coupled to the positive input of comparison amplifier 168 in comparator 62. The voltage coupled to summing resistors 154 and 158 are summed at summing junction 164, and the summed voltage is amplified and inverted by amplifier 170 and coupled to the negative input of comparison amplifier 172 in comparator 60.

The analog memory voltage developed by memory circuit 30 is coupled to the negative input of comparison amplifier 168 and the positive input of comparison amplifier 172. The operation of comparison amplifiers 168 and 172 has been described previously with respect to comparators 60 and 62 in FIG. 3.

The outputs of comparators 60 and 62 are coupled to NAND gate 74, and the output of NAND gate 74 is coupled to one input of NAND gates 174 and 176. An oscillator 179 is coupled through a switching transistor 181 to a second input of NAND gate 176 and a switch 46a, which is part of switch 46, is connected to the second input of NAND gate 174. A source of voltage is also connected to the second input of NAND gate 174.

As previously explained, if the pressure sensed either exceeds or falls below the windows established by the level set in pressure variation selection circuit 70, one of the comparators 60 or 62 develops a low state signal at its output which is coupled to NAND gate 74. If a low state signal is presented at either input to NAND gate 74, it develops a high state signal at its output which is coupled to one input of NAND gates 174 and 176. In normal operation when a high state signal is coupled to NAND gate 174 from NAND gate 74, the output of NAND gate 174 switches from a high state signal to a low state signal. Inverter 178 inverts this signal so that a high state signal is developed at the output of inverter 178 and coupled through diode 180 to any type of audible alarm desired so that an audible indication of a malfunction is provided. The output also is coupled to the blood pump in order to stop further operation thereof.

Switch 46a, which is part of switch 46, when closed operates as an override. The override position of switch 46 is shown clearly in FIG. 2. When closed, switch 46a couples a low state signal to the second input of NAND gate 174, forcing the output thereof to change to and maintain a high state signal as long as switch 46a is closed. With the high state signal developed at the output of NAND gate 174, a low state signal is developed at the output of inverter 178 and coupled through diode 180 to the alarm and pump. The presence of a low state signal will terminate the audible alarm and allow continued operation of the pump, thus allowing continued blood pumping during investigation of the cause of pressure change and preventing unnecessary shock to the patient.

The high state signal developed at the output of NAND gate 74 in response to exceeding or falling below the window limits established by pressure variation selection circuit 70 is also coupled to one input of NAND gate 176. The clock pulses from oscillator 179, are coupled through switching transistor 181 to the second input of NAND gate 176, causing NAND gate 176 to switch states changing from high to low state signals at its output at the clock pulse rate. Switching at the output of the NAND gate 176 will cause transistors 182 and 184 to switch at a corresponding rate. Light bulbs 186 connected to transistor 184 will be turned on and off at the clock rate by the switching of transistor 184, thus providing an additional indication of the alarm condition.

Figure 5:
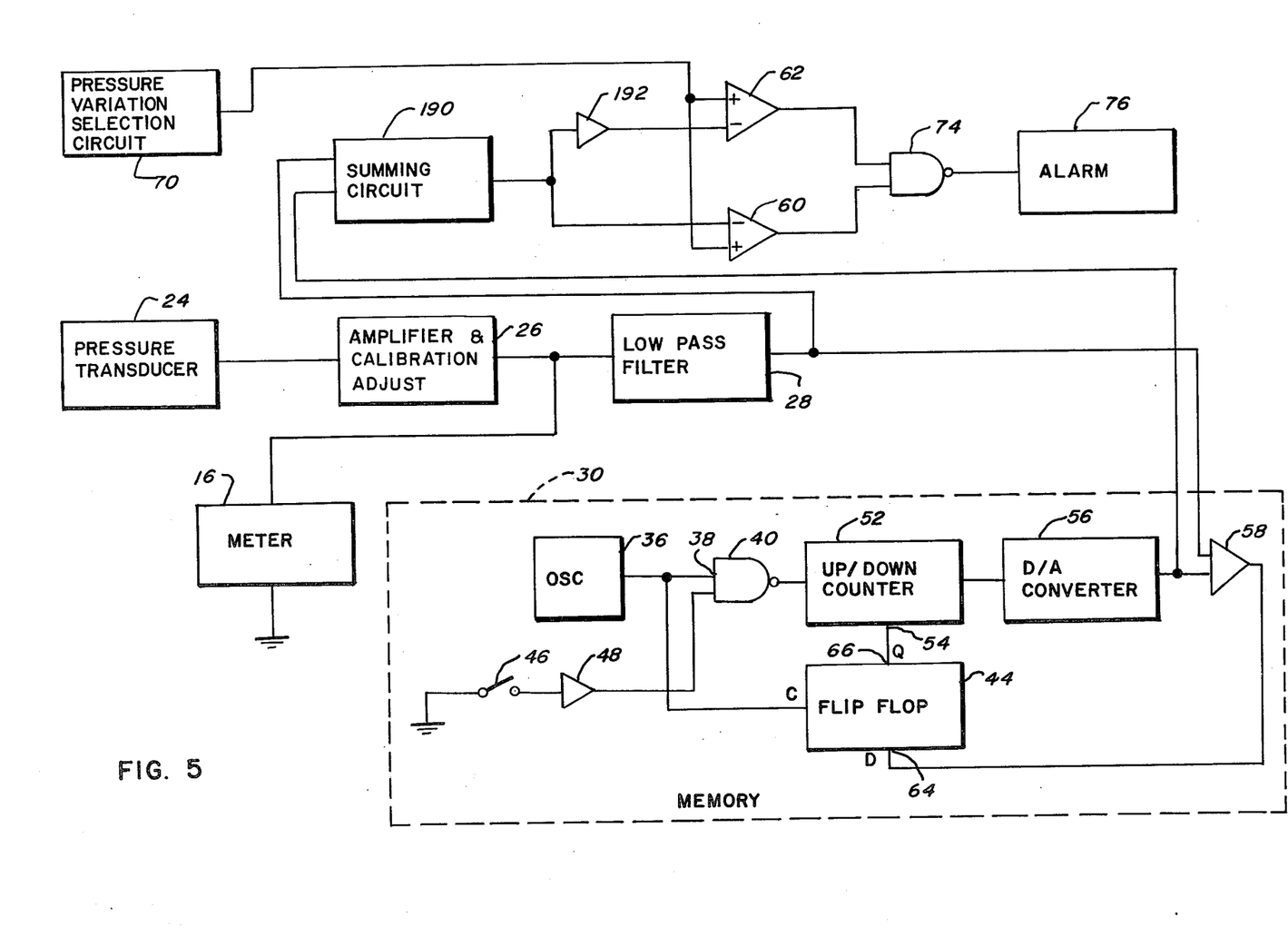
FIG. 5 is a block diagram of another embodiment of the alarm circuit of this invention.

Referring now to FIG. 5, a second embodiment of the alarm circuit of the invention is shown. A number of elements in the first and second embodiments of this invention are the same. Those elements which are the same have been identified with common numbers, and as they have previously been described with respect to FIGS. 3 and 4, will not be described again.

The analog memory voltage developed by memory 30 in this embodiment is coupled to one input of summing circuit 190, and the pressure voltage developed at the output of low pass filter 28 is coupled to the second input of summing circuit 190. Summing circuit 190 sums the two voltages together and couples a summed inverted voltage to the negative input of comparator 60 and through inverter 192 to the negative input of comparator 62. The output of pressure variation selection circuit in this embodiment is coupled to the positive input of comparator 62 and the positive input of comparator 60.

The voltage coupled from digital memory 30 is a negative voltage, and the voltage coupled from low pass filter 28 is a positive voltage, so that these voltages are subtracted from one another in summing circuit 190. If the pressure sensed by the pressure transducer 24 decreases, the voltage coupled from low pass filter 28 to summing circuit 190 will decrease resulting in a positive increase in the summed voltage coupled through summing circuit 190 to the negative input of comparator 60. When the voltage coupled to the negative input increases above the voltage coupled from pressure variation selection circuit 70 to the positive input of comparator 60, comparator 60 changes states and develops a low state signal at its output, causing NAND gate 74 to change states and develop a high state signal at its output for operating the alarm 76.

If the pressure sensed by pressure transducer 24 increases, the voltage coupled to summing circuit 190 increases, causing a negative increase in the voltage developed at the output of summing circuit 190. The negative increasing voltage is inverted by inverter 192, and the positive increasing voltage is coupled to the negative input of comparator 62. When the voltage coupled to the negative input of comparator 62 increases above the voltage coupled from pressure variation selection circuit 70 to the positive input of comparator 62, thus indicating a rise in pressure above the upper pressure limit, comparator 62 changes states and develops a low state signal at its output which is coupled to NAND gate 74. This low state signal causes the NAND gate 74 to change states and develop a high state signal at its output for operating alarm circuit 76.

Figure 6:
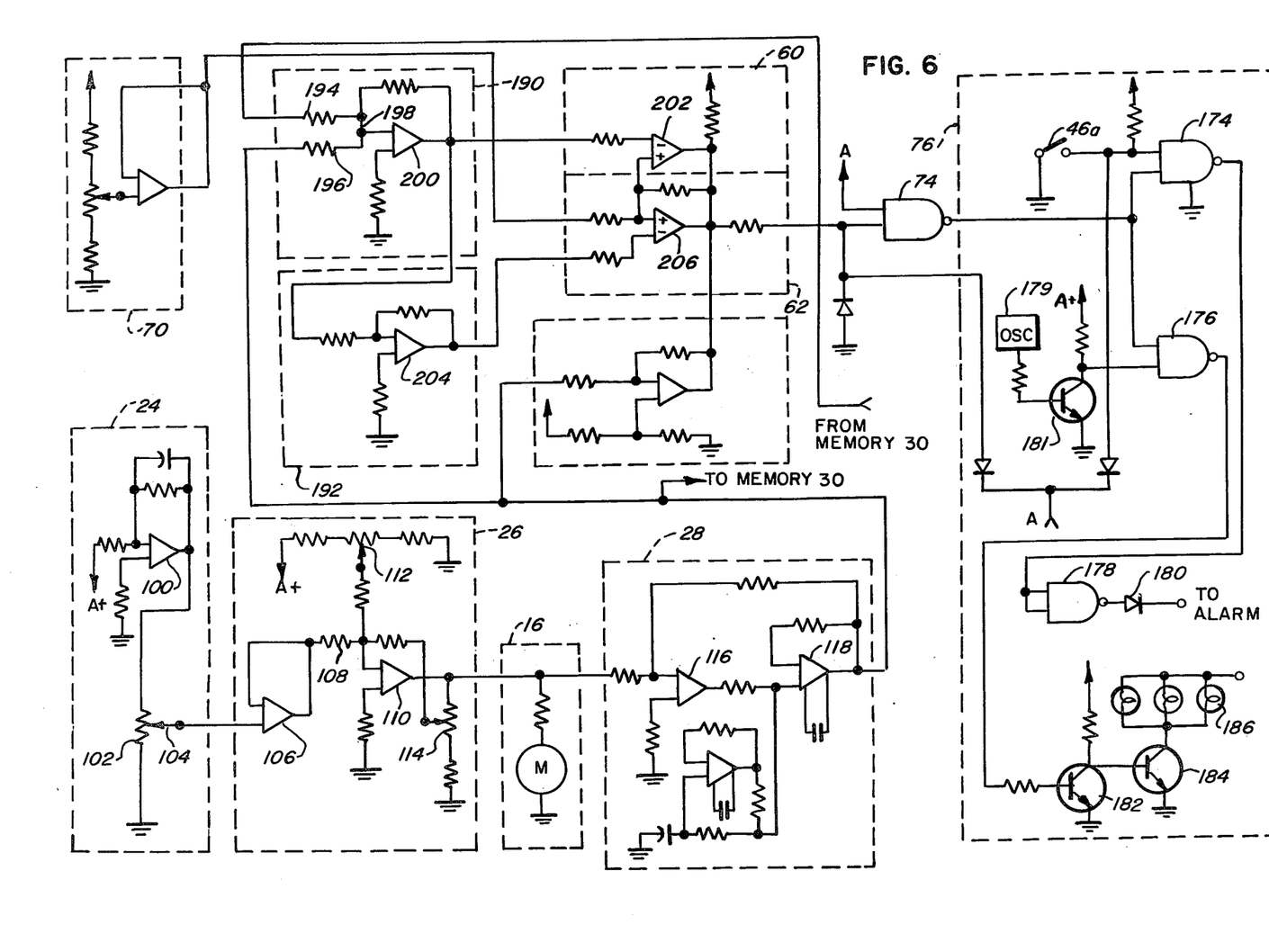
FIG. 6 is a schematic diagram of a portion of the alarm circuit represented in block diagram form in FIG. 5.

Referring now to FIG. 6, the output of memory circuit 30 is coupled to summing resistor 194 in summing circuit 190, and the pressure voltage at the output of low pass filter 28 is coupled to summing resistor 196. The two voltages are summed at summing junction 198, and the summed voltage is inverted by amplifier 200 and coupled to one input of comparison amplifier 202 in comparator 60. The output of amplifier 200 is also coupled to amplifier 204 in inverter 192; the output of amplifier 204 in inverter 192 is coupled to one input of comparison amplifier 206 in comparator 62. In this embodiment the outputs of comparison amplifiers 202 and 206 are connected together and to one input of NAND gate 74, however, the operation is the same as previously described.

While the present invention has been described by reference to specific examples, it is to be understood that modifications may be made by those skilled in the art without actually departing from the invention shown and described herein. It is therefore intended that the appended claims cover all variations that fall within the scope and spirit of this invention.

What is claimed is:

1. In a dialysis machine an alarm means operative in response to blood pressure changes to operate, said alarm means including in combination:
   blood pressure sensing means operative to develop a pressure signal which varies in accordance with blood pressure;
   memory means operative to receive said pressure signal, said memory means including storage means for storing said received pressure signal in digital form as a digital signal, and means coupled to said storage means operative in response to said stored digital signal to develop a memory signal;
   pressure variation selection means operative to develop a variation signal representing blood pressure variation limits;
   comparison means coupled to said sensing means, memory means and pressure variation selection means and operative in response to said pressure signal greater than said memory signal plus said variation signal to develop a first comparison signal and operative in response to said pressure signal less than said memory signal minus said variation signal to develop said first comparison signal; and
   control circuit means coupled to said comparison means and operative in response to said first comparison signal to operate for providing an alarm, said means coupled to said storage means including digital to analog converter means coupled to said storage means and operative to receive said digital signal from said storage means and to develop an analog memory signal, said memory means further including second comparison means coupled to said digital to analog converter means for comparing said analog memory signal and said pressure signal and developing a second comparison signal in accordance with the difference therebetween, and logic circuit means coupled to said storage means and said second comparison means and operative in response to said second comparison signal to vary said digital signal, said logic means including an oscillator for developing clock signals, gate means selectively operative to couple said clock signals to said storage means, and bistable means coupled to said second comparison means and operative in response to a second comparison signal having a first value to develop a first bistable signal and a second comparison signal having a second value to develop a second bistable signal, said storage means including counter means for storing said digital signal, said counter means coupled to said gate means and bistable means and operative in response to selective operation of said gate means to count said clock signals and vary said stored digital signal, said counter means counting up in response to said first bistable signal and down in response to said second bistable signal.

2. The dialysis machine of claim 1, wherein said memory means is selectively operative to receive said pressure signal and store a digital signal corresponding to said pressure signal.

3. The dialysis machine of claim 1, wherein said memory means includes switch means for selectively actuating said memory means to store said digital signal.

4. The dialysis machine of claim 1, wherein said blood pressure sensing means includes a pressure transducer for developing a pressure signal which varies in accordance with blood pressure, calibration adjustment means coupled to said pressure transducer for adjusting a minimum and maximum pressure signal, meter means coupled to said calibration adjustment means and operative in response to said pressure signal to provide an output indicating of said blood pressure, and filter means coupled to said calibration adjusting means for filtering undesired signals from said pressure signal.

5. In a dialysis machine an alarm means operative in response to blood pressure changes to operate, said alarm means including in combination:
   blood pressure sensing means operative to develop a pressure signal which varies in accordance with blood pressure;
   memory means operative to receive said pressure signal, said memory means including storage means for storing said received pressure signal in digital form as a digital signal and means coupled to said storage means and operative in response to said stored digital signal to develop a memory signal;
   pressure variation selection means operative to develop a variation signal representing blood pressure variation limits;
   comparison means coupled to said sensing means, memory means and pressure variation selection means and operative in response to said pressure signal greater than said memory signal plus said variation signal to develop a first comparison signal and operative in response to said pressure signal less than said memory signal minus said variation signal to develop said first comparison signal;
   said comparison means including, summing circuit means coupled to said pressure variation selection means for developing a first summing signal varying in accordance with said variation signal plus said pressure signal, and a second summing signal varying in accordance with said variation signal minus said pressure signal, and comparison circuitry coupled to said summing circuit means and said memory means and operative in response to a correlation between one of first and second summing signals and said memory signal to develop said first comparison signal, and
   control circuit means coupled to said comparison means and operative in response to said first comparison signal to operate for providing an alarm.

6. The dialysis machine of claim 5, wherein said summing circuit means includes a first summing circuit for developing said first summing signal and a second summing circuit for developing said second summing signal, said comparison circuitry including a first comparator coupled to said first summing circuit and said memory means and operative in response to a correlation between said first summing signal and said memory signal to develop said first comparison signal, and a second comparator coupled to second summing circuit and said memory means and operative in response to a correlation between said second summing signal and said memory signal to develop said second comparison signal.

7. In a dialysis machine an alarm means operative in response to blood pressure changes to operate, said alarm means including in combination:
   blood pressure sensing means operative to develop a pressure signal which varies in accordance with blood pressure;
   memory means operative to receive said pressure signal, said memory means including storage means for storing said received pressure signal in digital form as a digital signal and means coupled to said storage means and operative in response to said stored digital signal to develop a memory signal;
   pressure variation selection means operative to develop a variation signal representing blood pressure variation limits;
   comparison means coupled to said sensing means, memory means and pressure variation selection means and operative in response to said pressure signal greater than said memory signal plus said variation signal to develop a first comparison signal and operative in response to said pressure signal less than said memory signal minus said variation signal to develop said first comparison signal;
   said comparison means including, summing circuit means coupled to said pressure sensing means and said memory means for summing said blood pressure signal and memory signal to develop a summing signal, and comparison circuitry coupled to said summing means and to said pressure variation selection means and operative in response to a correlation between said variation signal and said summing signal to develop said first comparison signal, and
   control circuit means coupled to said comparison means and operative in response to said first comparison signal to operate for providing an alarm.

* * * * *